United States Patent [19]

Freudenberg et al.

[11] Patent Number: 4,900,479
[45] Date of Patent: Feb. 13, 1990

[54] PREPARATION OF CARBONYL HALIDES OF MORE THAN 7 CARBON ATOMS

[75] Inventors: Enrique Freudenberg, Limburgerhof; Peter Wittmer, Frankenthal; Andreas Hohmann, Ludwigshafen; Hans-Heinrich Bechtolsheimer, Dittelsheim-Hessloch, all of Fed. Rep. of Germany

[73] Assignee: BASF Aktiengesellschaft, Ludwigshafen, Fed. Rep. of Germany

[21] Appl. No.: 205,160

[22] Filed: Jun. 10, 1988

[30] Foreign Application Priority Data

Jun. 12, 1987 [DE] Fed. Rep. of Germany ....... 3719640

[51] Int. Cl.$^4$ ............................................... C11C 3/00
[52] U.S. Cl. .................................. 260/408; 562/861
[58] Field of Search .............. 260/408, 544 L, 544 D, 260/544 Y

[56] References Cited

U.S. PATENT DOCUMENTS 1,936,739 11/1933 Townsend ...................... 260/544 X
2,262,431 11/1941 Ralston et al. ...................... 260/408

FOREIGN PATENT DOCUMENTS 0153867 2/1982 German Democratic Rep. .
8203379 6/1982 Sweden .

*Primary Examiner*—Werren B. Lone
*Assistant Examiner*—Vera C. Clarke
*Attorney, Agent, or Firm*—John H. Shurtleff

[57] ABSTRACT

Carbonyl halides of the general formula I

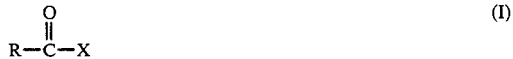

where R is an organic radical of more than 7 carbon atoms and X is chlorine or bromine, are prepared by reacting carboxylic acids of the general formula II

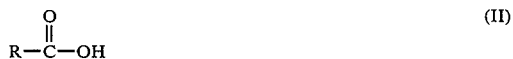

where R has the abovementioned meaning, with phosphorus chlorides or bromides by treating these reaction mixtures with carboxamide/hydrochloride or hydrobromide mixtures which are not homogeneously miscible with the carbonyl halides I and then separating off the carboxamide hydrochloride or hydrobromide phase.

17 Claims, No Drawings

PREPARATION OF CARBONYL HALIDES OF MORE THAN 7 CARBON ATOMS

The present invention provides a novel and improved process for preparing carbonyl chlorides or bromides of more than 7 carbon atoms by reacting the corresponding carboxylic acids with phosphorus chlorides or bromides.

Carbonyl halides are important intermediates in the synthesis of a large number of chemical products, for example drugs, surfactants or pulp sizing agents for paper. Industry is interested in particular in carbonyl chlorides.

The preparation of carbonyl chlorides by reacting carboxylic acids with phosphorus chlorides such as phosphorus pentachloride or phosphorus trichloride is long known, the reaction with phosphorus trichloride being more advantageous for economic reasons, since in the case of the pentachloride only 20% of the chlorine is utilized for carbonyl chloride formation. The acyl chlorides obtained are in general purified by distillation, with unconverted starting materials such as the acid and the phosphorus trichloride and byproducts of the reaction such as carboxylic anhydrides, phosphonocarboxylic anhydrides and other anhydrides of carboxylic acid and phosphorous acid being separated from the desired product in the first cut or as distillation residues. These impurities can have a strong adverse effect on the processing properties of the acyl chlorides.

Such a distillation in the case of longer-chain carbonyl chlorides is associated on account of the high boiling points of these products with substantial hardware requirements and with losses due to thermal decomposition. In addition, the decomposition products must be disposed of.

DD Patent 0,153,867 describes a two-stage process for preparing carbonyl chlorides by reacting acids, for example fatty acids, with phosphorus trichloride or thionyl chloride in the presence or absence of hydrogen chloride, whereby the product are obtained in improved purity without a distillative purification.

However, the batchwise processes described therein, after residence times of not less than eight days, give products which still contain several percent each of unconverted acid and acid anhydride as byproducts. The continuous processes give better products, but require the use of more complicated and expensive hardware, such as two kettle cascades connected in series with downstream separating vessels.

Swedish Application No. 82/03,379 of June 1, 1982 describes the conversion of carboxylic acids, in particular palmitic acid and ethylhexanoic acid, into acyl chlorides by reaction with phosphorus trichloride and aftertreatment of the crude acyl chloride with phosgene or thionyl chloride.

This gives, without distillation, acyl chlorides having a unconverted acid content of 0.3% or less.

However, the disadvantages of this process are the problems associated with the second halogenating agent, for example the safety requirements necessary for the handling of phosgene or the disposal of the sulfur dioxide formed in consequence of using thionyl chloride. Moreover, there is a risk of contaminating the carbonyl chloride with dark-colored and malodorous organosulfur impurities.

It is an object of the present invention to provide a better route to carbonyl chlorides and bromides of more than 7 carbon atoms and to overcome the disadvantages of the existing processes.

We have found that this object is achieved with a novel and improved process for preparing a carbonyl halide of the general formula I

where R is an organic radical of more than 7 carbon atoms and X is chlorine or bromine, by reacting a carboxylic acid of the general formula II

where R has the abovementioned meaning, with a phosphorus chloride or bromide, which comprises treating this reaction mixture with a carboxamide/hydrochloride or hydrobromide mixture which is not homogeneously miscible with the carbonyl halide I, and then separating off the carboxamide hydrochloride or hydrobromide phase.

It is essential for the success of the process according to the invention that the carboxamide hydrochloride or hydrobromide used is not homogeneously miscible with the carbonyl halide I formed, thereby making it possible to separate off the end product by simple phase separation of the reaction mixture present after the treatment. Furthermore, the two-phase method permits the simple recycling of the carboxamide hydrohalide phase for further aftertreatments.

Apart from the absence of homogeneous miscibility with the product there are no restrictions whatsoever as regards the choice of carboxamide hydrochloride or hydrobromide. However, in the preparation of carbonyl chlorides or bromides it will be convenient to use carboxamide hydrochlorides or hydrobromides which are for example preparable in situ from the carboxamide and hydrogen chloride or bromide. Suitable carboxamides are those of low molecular weight carboxylic acids such as butyric acid, propionic acid, acetic acid or formic acid and primary or secondary amines such as alkylamines, dialkylamines, N-methylaniline or piperidine. Preferred amides are those of the general formula III

where $R^1$ is hydrogen, methyl, ethyl, propyl, isopropyl or butyl, and $R^2$ and $R^3$ are each hydrogen, $C_1$–$C_4$-alkyl, $C_5$- or $C_6$-cycloalkyl, benzyl or phenyl, or $R^2$ and $R^3$ are linked together to form a $C_4$- or $C_5$-alkylene bridge, i.e. together with the nitrogen form a 5- or 6-membered ring.

To prepare carbonyl chlorides or bromides I of more than 7 carbon atoms, it is particularly advantageously possible to use N,N-dialkylformamide hydrochlorides of fewer than 8 carbon atoms. Examples are N,N-dimethylformamide, N,N-diethylformamide, N-methylformamide, N-ethylformamide, N,N-dipropylformamide and N,N-diisopropylformamide, of which N,N-dimethylformamide is particularly preferred because of its easy availability.

In general, catalytic amounts of the carboxamide, based on carboxylic acid used, are sufficient. It is possible to use for example amounts of from 0.5 to 100 mol-%, in particular of from 2 to 20 mol-%, based on carboxylic acid II. Larger amounts are possible, but in general do not produce any further benefits.

The aftertreatment as exemplified with carbonyl chloride is conveniently carried out by adding the carboxamide to the reaction mixture present after the chlorination and then adding hydrochloric acid in gaseous or liquid form. The hydrochloric acid can be added, based on the N,N-dialkylcarboxamide, in molar ratios of from 0.5:1 to 3:1, preferably in a molar ratio of from 1:1 to 2:1. The resulting two-phase mixture is thoroughly stirred and at the end separated into the two phases. The procedure is essentially the same with carbonyl bromides. The temperature is in general within the range in which the chlorination or bromination was carried out, for example at from 20° to 70° C., in particular at from 30° to 60° C.

The halogenation of the carboxylic acid is carried out in a conventional manner, making further comments superfluous.

The term carboxylic acid as used herein applies to any acid which, in accordance with the general definition, normally forms acyl halides on reaction with phosphorus-containing chlorinating or brominating agents such as phosphorus chlorides, for example phosphorus pentachloride and phosphorus trichloride, or phorphorus bromides, for example phosphorus tribromide. The process of the invention can be used for example in the chlorination or bromination of customary aliphatic carboxylic acids which contain higher or lower molecular weight aliphatic groups and on monoesters of dicarboxylic acids ketoacids etc. The process of the invention is preferably suitable for preparing acyl halides of aliphatic carboxylic acids, specifically in particular of monocarboxylic acids, i.e. for preparing compounds of the general formula I

(I)

where R is aliphatic hydrocarbyl which can be straight-chain or branched, saturated or olefinically or acetylenically unsaturated. Particular preference is given to aliphatic carboxylic acids of from 8 to 28, in particular of from 12 to 22, carbon atoms.

The reaction of carboxylic acid II, for example with phosphorus trichloride, can advantageously be carried out, at from 20° to 70° C., preferably at from 40° to 60° C., by initially charging the carboxylic acid or the phosphorus trichloride, in the presence or absence of an inert solvent, and adding the acid or phosphorus trichloride, in bulk or diluted with the same inert solvent. It is also possible to add carboxylic acid and chlorinating agent simultaneously. Phosphorus trichloride can be used in mixing ratios of from 1 mole of carboxylic acid:0.4 mole of phosphorus trichloride to 1 mole of carboxylic acid:0.8 mole of phosphorus trichloride, a ratio of from 1:0.5 to 1:0.6 being preferred.

The inert solvent can comprise hydrocarbons, halogenated hydrocarbons, for example chlorohydrocarbons, or ethers; preference is given to aromatic hydrocarbons such as toluene or xylenes.

On completion of the addition of carboxylic acid II or phosphorus trichloride, standing and removal of the phosphorous acid formed as per the following reaction equation:

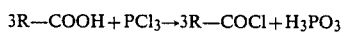

the reaction mixture can be subjected with uninterrupted, intermittent or even without stirring to a secondary reaction in which, at the end or else repeatedly in between, precipitated phosphorous acid, which is useful for other syntheses, can be separated off.

The further working-up in the aftertreatment according to the invention comprises separating the two liquid phases, of which the carboxamide hydrochloride or hydrobromide phase, with or without addition of hydrogen chloride or hydrogen bromide, can advantageously be reused for further aftertreatments and the phase which contains the carbonyl halide is stripped of volatile constituents such as excess phosphorus halide and any solvent in a conventional manner, for example by distillation at atmospheric or slightly reduced pressure, while the temperature should be below the decomposition temperature of the carbonyl halide I, advantageously below about 75° C.

The recovered solvent/phosphorus halide mixture can be reused for further reactions. The sparingly volatile carbonyl halide residue can contain residual levels of the inert solvent within the range from 2 to 5% which do not interfere, in particular in processing to secondary products in the presence of the same solvent, and if desired can be recovered at a subsequent stage.

The process according to the invention makes it possible to obtain very pure carbonyl halides containing less than 0.1% of unconverted carboxylic acid, less than 1% of carboxylic anhydride and only trace amounts of phosphorus-containing impurities.

In what follows, the invention is illustrated by Examples; the parts and percentages are by weight, unless otherwise stated.

EXAMPLE 1

(Comparative Example)

A reaction vessel which is equipped with a stirrer, heating means and a bottom outlet is charged in the absence of moisture with 275 parts of phosphorus trichloride and 300 parts of anhydrous toluene and heated to 40° C. 1,100 parts of molten technical grade stearic acid are then added with stirring in the course of 5 hours during which the temperature is maintained at from 40° to 45° C. After a brief settling period the deposited phosphorous acid is separated off, and the reaction mixture is stirred at 40° C. for a further 2 hours. After another brief settling period the further quantity of phosphorous acid which has precipitated out is separated off.

Unconverted phosphorus trichloride and excess solvent are distilled off under a reduced pressure of 25 mbar at a substance temperature of not more than 75° C. until nothing more passes over. This stearoyl chloride, which still contains 1.5% of toluene, is found to have the following analytical data (calculated for 100% pure, toluene-free product):

90.1% of stearoyl chloride, <1% of stearic acid, 4.1% of stearic anhydride, <0.05% of phosphorus trichloride, 370 ppm of phosphorus.

EXAMPLE 2

(Comparative Example)

Example 1 is repeated to produce a solution of stearoyl chloride in toluene. The concluding distillation is preceded by introducing 20 mol-%, based on starting stearic acid, of hydrochloric acid in gaseous form with stirring at from 40° to 45° C. into the reaction mixture in the course of one hour. Thereafter the volatiles are distilled off as described in Example 1.

This acyl chloride, which still contains 2.4% of toluene, is found to have the following analytical data (calculated for 100% pure, toluene-free product): 91.3% of stearoyl chloride, <1% of stearic acid, 4.1% of stearic anhydride, <0.05% of phosphorus trichloride, 600 ppm of phosphorus.

EXAMPLE 3

Example 1 is repeated to produce a solution of stearoyl chloride in toluene. The concluding distillation is preceded by adding 10 mol-% of dimethylformamide and, at from 40° to 45° C., passing 20 mol-% of hydrochloric acid (mol-%ages all based on starting stearic acid) in gaseous form with stirring into the reaction mixture in the course of one hour. A second phase forms, which is not miscible with the stearoyl chloride solution in toluene. The two-phase mixture is thoroughly stirred at from 40° to 45° C. for 2 hours, and the dimethylformamide hydrochloride phase is then separated off. Thereafter the volatiles are distilled off as described in Example 1. This acyl chloride, which still contains 2.6% of toluene, is found to have the following analytical data (calculated for 100% pure, toluene-free product):

96.0% of stearoyl chloride, <1% of stearic acid, <1.0% of stearic anhydride, <0.05% of phosphorus trichloride, 1,400 ppm of phosphorus, 150 ppm of total nitrogen.

EXAMPLE 4

Example 1 is repeated to produce a solution of stearoyl chloride in toluene. The concluding removal of volatiles by distillation is preceded by adding the dimethylformamide hydrochloride phase from Example 3 and then passing in 20 mol-%, based on starting stearic acid, of hydrochloric acid in gaseous form at from 40° to 45° C. in the course of one hour. The two-phase mixture is thoroughly stirred at that temperature, and the dimethylformamide hydrochloride phase is then separated off. Thereafter the volatiles are distilled off as described in Example 1. This acyl chloride, which still contains 2.7% of toluene, is found to have the following analytical data (calculated for 100% pure, toluene-free product):

94.6% stearoyl chloride, <0.1% of stearic acid, <1.0% of stearic anhydride, <0.05% of phosphorus trichloride, 630 ppm of phosphorus.

We claim:

1. In a process for preparing a carbonyl halide of the formula $$R-\underset{\underset{O}{\|}}{C}-X \qquad (I)$$

where R is an organic radical of more than 7 carbon atoms and X is chlorine or bromine, by chlorinating or brominating a carboxylic acid of the formula $$R-\underset{\underset{O}{\|}}{C}-OH \qquad (II)$$

where R has the abovementioned meaning, in a reaction with a phosphorus chloride or bromide, the improvement which comprises:

treating the reaction mixture obtained by said chlorination or bromination with a carboxamide/hydrochloride or hydrobromide mixture which is not homogeneously miscible with the carbonyl halide I, and then separating off the carboxamide hydrochloride or hydrobromide phase.

2. A process as claimed in claim 1, wherein the reaction mixture is treated with from 0.5 to 100 mol-% of a carboxamide/hydrochloride or hydrobromide mixture, based on starting carboxylic acid II.

3. A process as claimed in claim 1, wherein the reaction mixture is treated with a carboxamide/hydrochloride mixture.

4. A process as claimed in claim 1, wherein the reaction mixture is treated with formamide/hydrogen chloride.

5. A process as claimed in claim 1, wherein in the compound of the formula II R is an aliphatic radical of from 8 to 28 carbon atoms.

6. A process as claimed in claim 1, wherein the phosphorus chloride used is phosphorus trichloride.

7. A process as claimed in claim 1, wherein said reaction mixture is treated with from 2 to 20 mol-% of said carboxamide/hydrochloride or hydrobromide mixture, based on the starting carboxylic acid II.

8. A process as claimed in claim 1, wherein both the chlorinating or brominating step and the aftertreatment step are carried out at a temperature of about 20° to 70° C.

9. A process as claimed in claim 8, wherein both steps are carried out at about 30° to 60° C.

10. A process as claimed in claim 1, wherein reactant II is an aliphatic monocarboxylic acid of from 8 to 28 carbon atoms.

11. A process as claimed in claim 10 wherein said acid has from 12 to 22 carbon atoms.

12. A process as claimed in claim 1, wherein the step of chlorinating or brominating the carboxylic acid II is carried out in an inert solvent.

13. A process as claimed in claim 12, wherein the inert solvent is selected from the group consisting of hydrocarbons, halogenated hydrocarbons, ethers and aromatic hydrocarbons.

14. A process as claimed in claim 12, wherein the inert solvent is an aromatic hydrocarbon.

15. A process as claimed in claim 1, wherein the carboxamide is a compound of the formula $$R^1-CO-NR^2R^3$$

wherein $R^1$ is hydrogen or $C_1$–$C_4$-alkyl, and each of $R^2$ and $R^3$ is selected from the group consisting of hydrogen, $C_1$–$C_4$-alkyl, $C_5$- or $C_6$-cycloalkyl, benzyl or phenyl, or $R^2$ and $R^3$ when taken together form a $C_4$- or $C_5$-alkylene bridge with the nitrogen atom.

16. A process as claimed in claim 15, wherein the carboxamide is an N,N-dialkylformamide of fewer than 8 carbon atoms.

17. A process as claimed in claim 15, wherein the carboxamide is N,N-dimethylformamide.

* * * * *